United States Patent [19]
Van Venrooij

[11] Patent Number: 5,849,032
[45] Date of Patent: Dec. 15, 1998

[54] SINGLE PASS MEDICAL ELECTRICAL LEAD

[75] Inventor: Paulus Van Venrooij, Hoensbroek, Netherlands

[73] Assignee: Medtronic, Inc., Minneapolis, Minn.

[21] Appl. No.: 937,444

[22] Filed: Sep. 25, 1997

[51] Int. Cl.⁶ ............................................... A61N 1/05
[52] U.S. Cl. ........................ 607/123; 607/125; 607/126
[58] Field of Search .................... 607/116, 119, 607/122, 123, 125, 126, 130; 600/374, 375

[56] References Cited

U.S. PATENT DOCUMENTS

| | | |
|---|---|---|
| 4,057,067 | 11/1977 | Lajos . |
| 4,154,247 | 5/1979 | O'Neill . |
| 4,497,326 | 2/1985 | Curry . |
| 4,567,901 | 2/1986 | Harris . |
| 5,238,007 | 8/1993 | Giele et al. ............................ 607/126 |
| 5,545,206 | 8/1996 | Carson .................................. 607/126 |
| 5,628,778 | 5/1997 | Kruse et al. . |
| 5,653,742 | 8/1997 | Parker et al. ......................... 607/137 |

*Primary Examiner*—William E. Kamm
*Assistant Examiner*—George R. Evanisko
*Attorney, Agent, or Firm*—Michael J. Jaro; Harold Patton

[57] ABSTRACT

A single pass medical electrical lead featuring an atrial wall wedging mechanism which will permit the atrial electrodes to be positioned directly against the right atrial wall. In the preferred embodiment the atrial wall wedging mechanism comprises an extendible finger which may be used to wedge the lead body in the region where the inferior vena cava enters the right atrium and the right atrium empties through the tricuspid valve into the right ventricle. Through such wedging, the atrial electrodes may be caused to be positioned directly against the right atrium wall without causing excessive pressure to be communicated to the distal tip of the lead.

16 Claims, 5 Drawing Sheets

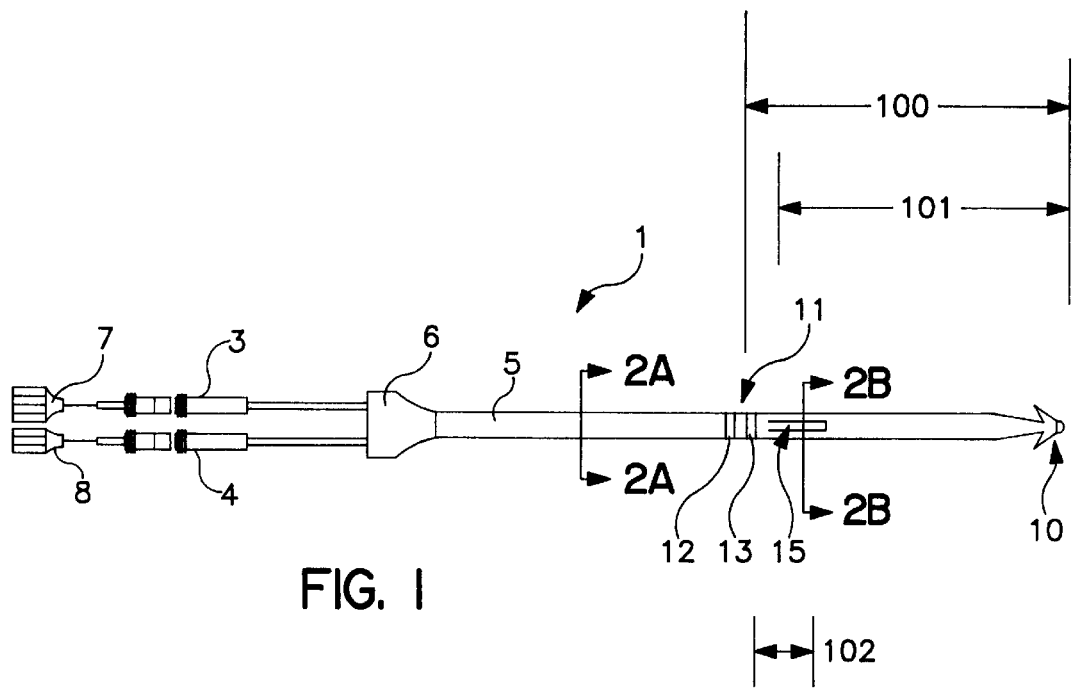
FIG. 1
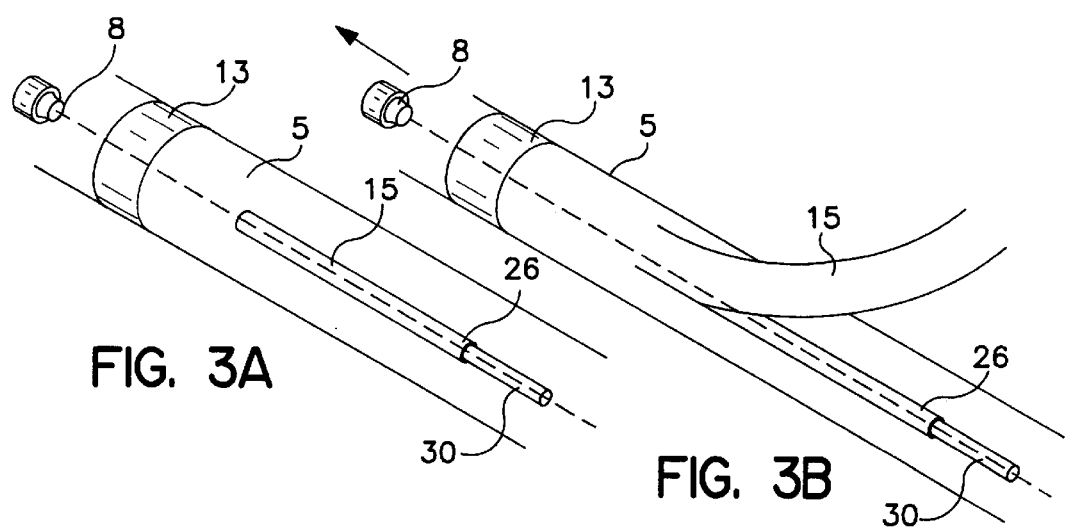
FIG. 3A
FIG. 3B

5,849,032

SINGLE PASS MEDICAL ELECTRICAL LEAD

FIELD OF THE INVENTION

This invention relates to the field of body-implantable medical device systems, and in particular to a body-implantable medical device system which includes a single pass medical electrical lead.

BACKGROUND OF THE INVENTION

Modern electrical therapeutic and diagnostic devices for the heart, such as pacemakers, cardioverters and defibrillators for example, require a reliable electrical connection between the device and a pre-selected region of the heart. Typically an electrical "lead" is used for the desired electrical connection.

One type of commonly used implantable lead is an endocardial lead. Endocardial leads are attached at their proximal end to an implantable pulse generator and at their distal end to the endocardium of a cardiac chamber. Such leads normally take the form of a long, generally straight, flexible, insulated conductor having one end electrically connected to the pulse generator and the other end electrically connected to the endocardium through an electrode. Among the many advantages of an endocardial lead is that it may be positioned into the heart by sliding the lead through a vein until the electrode is properly positioned, rather than physically exposing the heart itself.

The specific design of the endocardial lead used has often varied depending upon the region of the heart to which it is to be connected, in particular whether it is for a ventricular application or an atrial application.

Ventricular endocardial leads are often readily flexible and have tines or fins at their distal end. These tines are provided to engage the trabeculation within the ventricle so as to reliably fix, or at least position, the electrode in the desired location. Unlike the ventricles, the atrial walls are relatively smooth. Because the atrial walls are smooth it has been difficult to retain the electrode in a fixed position with respect to the wall of the atrium. One approach commonly used has been to form the distal end of an atrial lead in a J-shaped configuration. Such a configuration causes the distal end to curve upwardly once the lead is within the atrium so as to provide reliable contact between the electrode and the heart tissue.

In dual chamber pacing, however, it is necessary to establish an electrical connection with both chambers of the heart. Typically this now involves the placement of two leads, a ventricular lead as well as an atrial lead, within the patient's heart. Usually the ventricular lead is placed first, i.e. it is passed through a blood vessel and into the ventricular cavity. When the ventricular pacing lead has been stabilized within the heart, the second lead, or atrial lead, is passed through the blood vessel and is moved into a selected position within the atrial cavity.

The placement of two separate pacing leads into two separate chambers of the heart, however, is a relatively complicated procedure. First as the second lead is being inserted, it is possible to strike the first lead with the second lead thereby dislodging the first lead from its desired position. In addition, the presence of two leads may cause a significant decrease in blood flow through the blood vessel, especially in patients having relatively small diameter vessels. Finally, although transvenous placement of a lead is relatively not traumatic, it would nonetheless be beneficial to simplify and shorten the implant procedure as much as possible. Reducing the number of leads implanted from two to one would be of significant benefit.

Because of the difficulties encountered by placing two leads there has been a considerable number of past attempts to design a single lead which provides an electrical connection to both chambers of the heart, often referred to as a "single pass lead." An early attempt at a single pass lead was taught by Bures in U.S. Pat. No. 3,865,118. Because the configuration taught by Bures requires the ventricular lead to be coaxially mounted within the outer sheath, minimal control could be exercised over placement of the atrial electrodes. To compensate for this lack of control, Bures taught the use of opposing (i.e., spaced by 180 degrees) spring loaded electrodes. Such a placement technique is susceptible to dislodgement, however. It is also electrically inefficient because of the relatively large surface area of the electrode and the difficulty in controlling the amount of that surface area actually in contact with the atrial wall. Furthermore, using the outer catheter to control flexure of the atrial electrodes lead to sealing problems.

Lajos in U.S. Pat. No. 4,057,067 attempted to solve many of the control problems found with the lead taught by Bures by using a "J" shaped atrial lead with stylet control. Because the atrial and ventricular leads, however, were spaced a fixed distance, the lead taught by Lajos did not accommodate various sized hearts. The lead of Lajos has at least two additional drawbacks. First, the projection provided on the lead body into which the atrial component nests will give rise, over time, to an excessively large fibrotic sheath. In addition, because the lead body is not over uniform diameter, the removability of the lead will be vastly complicated. Finally, the atrial electrodes of Lajos are merely disposed from the lead and presented to the atrial tissue in a similar manner to any of the prior "J" shape leads. As is well known in the art, J shape leads are not satisfactory unless presented into the atrial appendage at the top of the right atrium.

A third single pass lead configuration was taught by Sabel in U.S. Pat. No. 3,949,757. Sabel used the "J" shaped atrial electrode placement as taught by Lajos but slid the atrial catheter within the outer sheath of the ventricular catheter. This solved one problem of Lajos by not requiring an aperture in the distal end of the atrial electrode for stylet straightening of the "J" shape. It did not completely solve the problem of differing heart sizes, however. The distance between the distal end of the atrial catheter and the distal end of the outer sheath was essentially fixed by practical factors even though the atrial catheter was slidably mounted within outer sheath because sliding of the atrial catheter also changed the shape of the "J". The atrial electrode may be lowered in the atrium by moving the atrial catheter either proximal or distal relative to the outer sheath. However, the atrial electrode may not be raised within the atrium. That distance is effectively established by the prior implantation of the ventricular electrode. Providing a larger distance between the ventricular electrode and the distal end of outer sheath would tend to distort the "J" shape of the atrial catheter.

Another proposed configuration for a single pass lead was disclosed by Gold in U.S. Pat. No. 4,444,195 which disclosed a flexible catheter having a series of ring electrodes selectively utilized for pacing and sensing in both chambers of the heart. As discussed above, one significant problem with this configuration was the reliable, consistent and acceptable placement of the atrial electrodes.

A still further attempt to configure a single pass lead was disclosed by Harris in U.S. Pat. No. 4,627,439 which featured a single pass lead having a pre-bent atrial section. In particular the atrial section had a bend with the electrodes positioned on the bend. The bend, it was taught would assist in properly maintaining the position of the atrial electrodes. The Harris design, however, failed to provide an acceptable single pass lead. In particular the configuration of the pre-bent section having electrodes on the bend failed to provide acceptable chronic electrode position.

A still further attempt to configure the single pass lead was disclosed by Kruse in U.S. Pat. No. 5,628,778. Kruse featured a lead having a reinforced pre-bent section of the lead body which was designed to wedge within the atrium, between the right wall of the atrium and the tricuspid valve, and thereby cause the atrial electrode assembly to be positioned directly against the right atrial wall. On occasion, however, such a design has proven difficult to properly position. Namely, to properly wedge the pre-bent reinforced portion of the lead body into position such that the atrial electrodes are properly and consistently positioned against the right atrial wall.

Besides all of the above noted problems, several past lead designs have further featured the problem of communicating excessive amounts of pressure to the distal tip of the lead, and thus to the ventricular tissue. In a chronic setting, because an electrode is often located in such a position, the excessive pressure causes excessive fibrosis to develop (or in rare cases puncturing of the cardiac wall) thereby diminishing the electrical characteristics of the system. As is well known, this may causes system failure as well as undue battery depletion.

Thus it is an object of the present invention to provide a single pass medical electrical lead which will consistently permit the electrodes to be placed directly against the right atrial wall without causing excessive pressure to be communicated to the distal tip of the lead.

SUMMARY OF THE INVENTION

The present invention is directed to a single pass medical electrical lead featuring an atrial wall wedging mechanism which will permit the atrial electrodes to be positioned directly against the right atrial wall. In the preferred embodiment the wall wedging mechanism comprises an extendible finger which may be used to wedge the lead body in the region where the inferior vena cava enters the right atrium and the right atrium empties through the tricuspid valve into the right ventricle. Through such wedging, the atrial electrodes may be caused to be positioned directly against the right atrium wall without causing excessive pressure to be communicated to the distal tip of the lead.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein it should be understood the drawings are not necessarily to scale.

FIG. 1 is a plan view of a lead according to the present invention.

FIGS. 3A and 3B show stages of the extension of finger.

DETAILED DESCRIPTION OF THE INVENTION

Figure 2A:
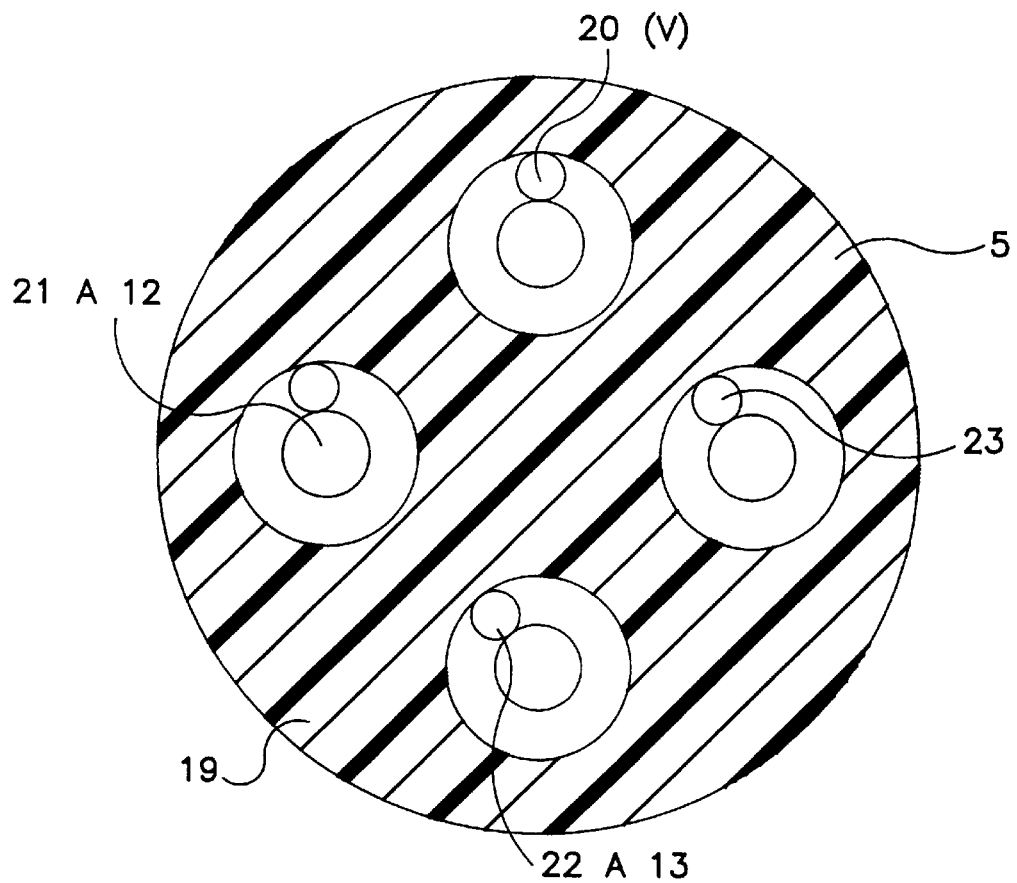
FIG. 2A is a cross sectional view of lead body 5 taken along the lines 2A—2A shown in FIG. 1.

The present invention is described within the context of a single pass bipolar transvenous endocardial lead adapted for use in connection with an implantable cardiac pulse generator, such as the Medtronic KAPPA™ or THERA™ as well as other models commercially available from Medtronic, Inc., Minneapolis, Minn. The present invention, however, may be advantageously practiced in conjunction with many different types of implantable medical devices as well as many other various embodiments of therapeutic or diagnostic catheters and is not limited only to medical electrical leads. For purposes of illustration only, however, the present invention is below described in the context of a transvenous endocardial lead.

FIG. 1 is a plan view of a lead according to the present invention. As seen, lead 1 features a pair of connector pin assemblies 3 and 4, electrically connected to a lead body 5 through a coupling 6. Also shown disposed in the connector pin assembly are a pair of stylets 7 and 8. Stylet 7 runs throughout the length of the lead body until a point proximate to ventricular electrode 10. Ventricular electrode 10 is of a standard design. Further details may be found in the U.S. Pat. No. 5,628,778 of Kruse incorporated herein by reference. Although shown as a unipolar electrode in the ventricle, a bi-polar electrode configuration may also be used. Atrial electrode assembly 11 features a pair of whole rings 12 and 13. Atrial electrode assembly may also be of any standardized design and further details may be found in the above-identified Kruse patent. Stylet 8 runs from connector pin assembly 4 through lead body and through finger 15, described in further detail below. As described below finger is used for wedging the lead body between the region where the inferior vena cava enters the right atrium and the right atrium empties through the tricuspid valve into the right ventricle and the right atrium wall thereby causing the atrial electrodes to be positioned directly against the right atrium wall. In order to permit such a wedging to be accomplished satisfactorily it is essential that there be the proper relationship between the finger and atrial electrodes. In particular, as seen finger is positioned a distance 101 between approximately 6 cm. and 10 cm. from the second end of the lead body while atrial electrode positioned a distance 100 between approximately 11 cm. and 16 cm. from the second end of the lead body. Finally finger has a length 102 between approximately 8 mm. and 15 mm. in length. Of course the exact dimensions selected will depend upon the size of the heart into which the lead is to be implanted.

FIG. 2A is a cross sectional view of lead body 5 taken along the lines 2A—2A shown in FIG. 1. As seen, lead body, preferably, is constructed of a polymer sheath 19 having a series of four lumens therein. Polymer sheath may be of any acceptable material, such as either silicone or polyurethane. Positioned within each of the lumens are coiled conductors 20–23. Conductors are provided to electrically communicate from the connector pin assembly to each of the electrodes shown and, in addition, to assist in the advent of finger 15. In particular, conductor 20 runs from connector pin assembly 3 to ventricular electrode 10. Conductors 21 and 22 run from connector pin assembly 4 to atrial electrodes 12 and 13 respectively. Conductors 20–22 are preferably a biocompatible conductor such as MP35N. Conductor 23 is provided to assist in the extension of finger 15, discussed in further detail below.

Figure 2B:
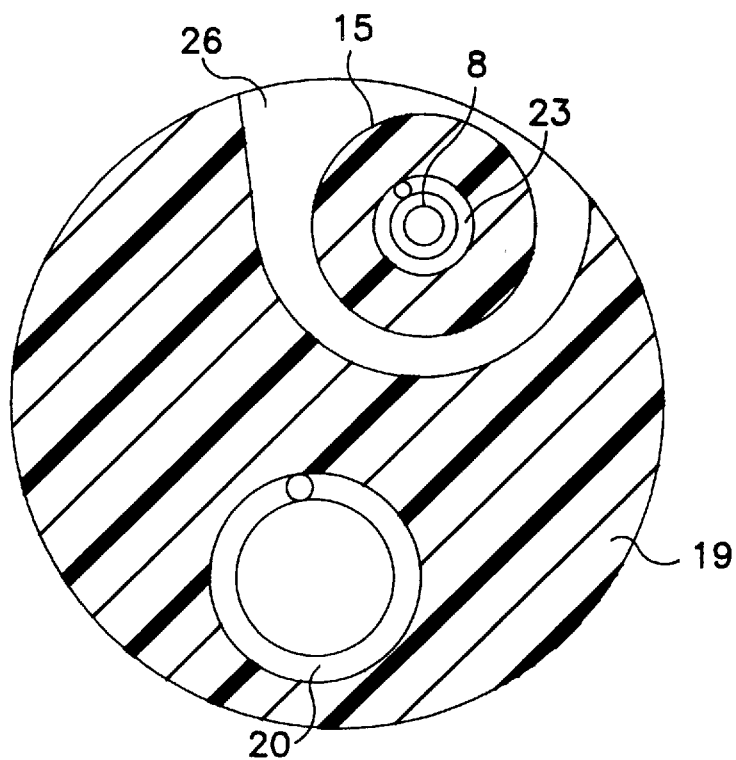
FIG. 2B is a cross sectional view of the lead shown in FIG. 1 taken along the lines 2B—2B.

FIG. 2B is a cross sectional view of the lead shown in FIG. 1 taken along the lines 2B—2B. This view shows, in detail, the relationship between the finger 15 and the lead body 19. As seen, lead body 19 has a furrow 26 into which finger 15 may be disposed. As also seen, conductor 23 is provided within finger 15. Conductor 23 is preferably a shape memory alloy, such as nitinol, and is designed to cause finger 15 to extend away from lead body and out of furrow. Stylet 7, however, is disposed within lumen of conductor 23 and completely through finger 15 to thereby cause finger to remain disposed within furrow 26.

FIGS. 3A and 3B show stages of the extension of finger 15. In FIG. 3A finger is shown captured within furrow 26 by stylet 8. In particular, stylet 8 extends through lead body and through the length of finger 15, exiting the finger and extending partially along furrow 26 and into stylet port 30. As seen, stylet port 30 has a lumen corresponding with style 8 to thereby capture stylet 8 and secure it therein.

In FIG. 3B the stylet 8 has been retracted out of stylet port 30 and out of finger 15. Due to the pre-shape provided to conductor 23 in the region of finger 15, once stylet 8 has been removed finger 15 extends out of furrow 26 and away from lead body 5.

Figure 4:
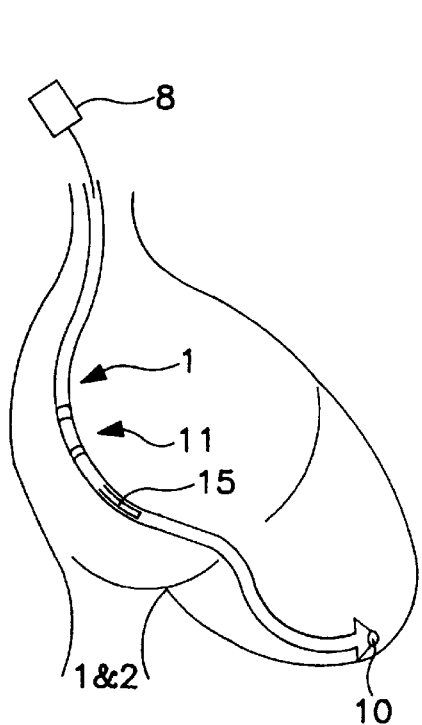
FIGS. 4–6 depict the various stages of implanting a lead into a heart.
Figure 5:
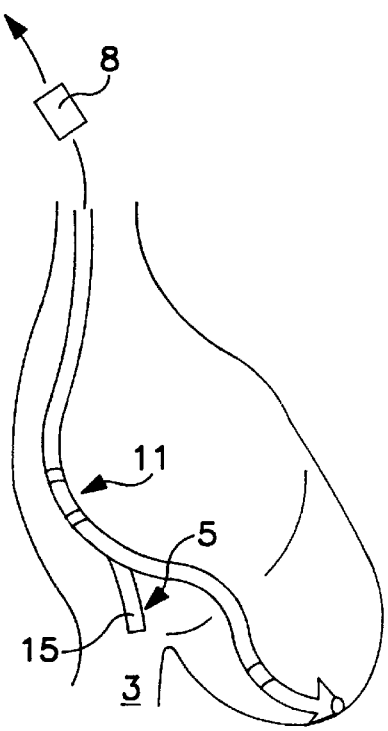
Figure 6:
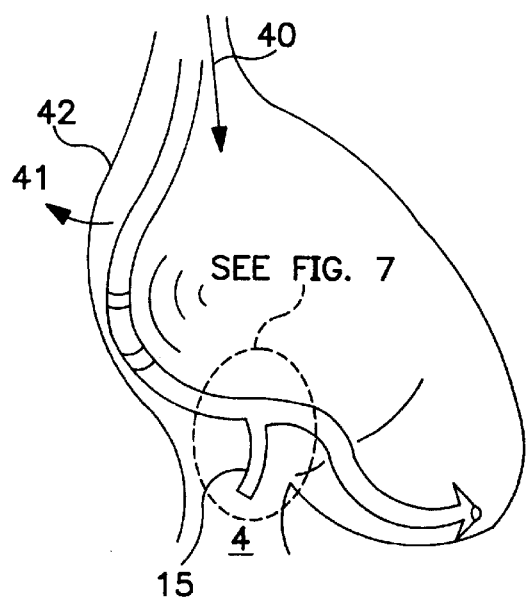

FIGS. 4–6 depict the various stages of implanting a lead into a heart. As seen, in FIG. 4 the lead 1 is introduced into the heart such that ventricular electrode 10 is positioned properly within the ventricular apex and sufficient electrical contact is made.

Turning now to FIG. 5, the atrial stylet 8 is retracted thereby resulting in the finger 15 to be deployed out from furrow 26 and away from lead body 5. Once the finger is deployed the lead body is further advanced in the direction 40 shown in FIG. 6 to thereby cause finger 15 to wedge against the area between where the inferior vena cava enters the right atrium and the right atrium flows through the tricuspid valve. As seen in this FIG., movement of the lead body in the direction 40 causes the lead body to bow out in the direction 41 due to the interaction of finger 15 with such tissue. Thus, the lead body cannot be advanced beyond where finger 15 permits it to be advanced, thereby any excessive lead body fed into the right atrium is caused to contact the right atrial wall 42 without causing excessive pressure to be communicated to the distal tip of the lead. One important feature of the finger is that it is both pliable and features a blunted tip. This configuration of bluntness and pliability ensure that the finger will no cause any untoward damage to the venous system once the finger is deployed.

Figure 7:
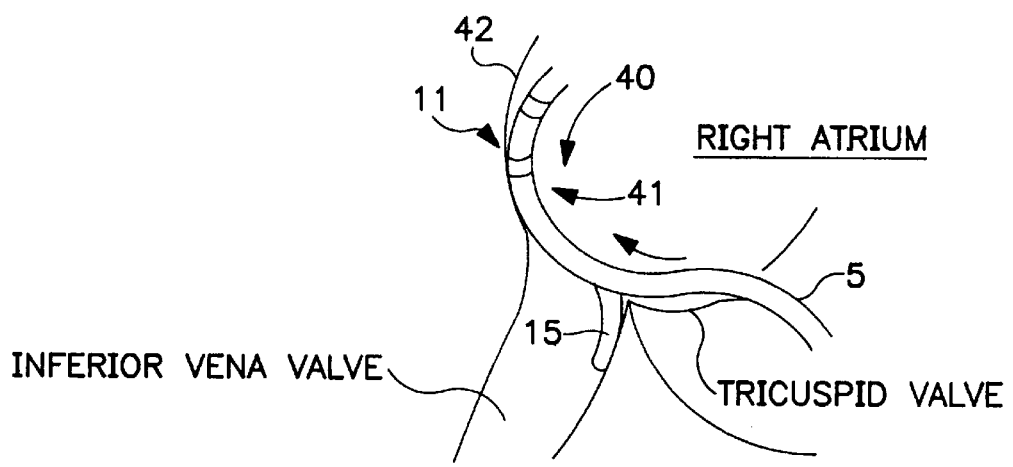
FIG. 7 depicts a detailed view of the interaction of finger with tissue and the resultant bowing of the lead body.

FIG. 7 depicts a detailed view of the interaction of finger 15 with such tissue and the resultant bowing of the lead body in the direction 41 due to the feeding of additional lead body into the right atrium.

It is to be understood that the present invention is not limited to use only in pacing leads, and may be employed in the construction of many of various type of therapeutic and diagnostic devices, including defibrillation leads, intended to be disposed within the coronary sinus. In fact, for the purposes of this specification and claims, the term "lead" is used herein in its broadest sense and includes any stimulation lead or sensing lead, a combination thereof or any other elongated member, such as a catheter, which may usefully be introduced into a body. For purposes of illustration only, however, the present invention has been described in the context of transvenous pacing lead.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A medical electrical lead assembly comprising:
   a connector assembly;
   a lead body having a first end and a second end, the first end coupled to the connector assembly, the lead body having an insulative sheath having an insulative sheath lumen and a conductor positioned within the insulative sheath lumen,
   an electrode coupled to the conductor and positioned at the second end of the lead body
   wherein the lead body further features a furrow within the insulative sheath and a finger extending from the insulative sheath and biased away from the sheath and out of the furrow, the finger having a pliable blunted tip wherein the finger is positioned between approximately 6 cm. and 10 cm. from the second end of the lead body.

2. A medical electrical lead assembly according to claim 1 wherein the lead assembly further having means for maintaining the finger within the furrow while the lead is being implanted and permitting the finger to bias away from the sheath and out of the furrow once the lead is implanted.

3. A medical electrical lead assembly according to claim 1 wherein the finger has a finger length and the furrow has a furrow length, the finger length less than the furrow length.

4. A medical electrical lead assembly according to claim 1 wherein the finger has a finger width and the furrow has a furrow width, the finger width less than the furrow width.

5. A medical electrical lead assembly according to claim 1 wherein the means for maintaining the finger within the furrow while the lead is being implanted and permitting the finger to bias away from the sheath and out of the furrow once the lead is implanted comprises a flexible hinge coupling the finger to the insulative sheath, the flexible hinge biasing the finger out of the furrow and away from the insulative sheath, the finger further comprising a stylet lumen communicating with the insulative sheath lumen.

6. A medical electrical lead assembly according to claim 1 wherein the lead assembly further features an atrial electrode coupled to the conductor and positioned proximal to the second end of the lead body, the atrial electrode positioned between approximately 11 cm. and 16 cm. from the second end of the lead body.

7. A medical electrical lead assembly according to claim 6 wherein the atrial electrode comprising a pair of whole ring electrodes.

8. A medical electrical lead assembly comprising;
   a connector assembly;
   a lead body having a first end and a second end, the first end coupled to the connector assembly, the lead body having an insulative sheath having a insulative sheath lumen and a conductor positioned within the insulative sheath lumen,
   a ventricular electrode coupled to the conductor and positioned at the second end of the lead body;
   an atrial electrode coupled to the conductor and positioned proximal to the second end of the lead body
   wherein the lead body further features means for wedging the lead body between the region where the inferior vena cava enters the right atrium and the right atrium empties through the tricuspid valve into the right ventricle thereby causing the atrial electrode to be positioned directly against the right atrium wall.

9. A medical electrical lead assembly according to claim 8 wherein the means for wedging comprise a furrow within the insulative sheath and a finger extending from the insulative sheath and biased away from the sheath and out of the furrow, the finger having a pliable blunted tip.

10. A medical electrical lead assembly according to claim 9 wherein the lead assembly further having means for maintaining the finger within the furrow while the lead is being implanted and permitting the finger to bias away from the sheath and out of the furrow once the lead is implanted.

11. A medical electrical lead assembly according to claim 10 wherein the finger has a finger length and the furrow has a furrow length, the finger length less than the furrow length.

12. A medical electrical lead assembly according to claim 11 wherein the finger has a finger width and the furrow has a furrow width, the finger width less than the furrow width.

13. A medical electrical lead assembly according to claim 10 wherein the means for maintaining the finger within the furrow while the lead is being implanted and permitting the finger to bias away from the sheath and out of the furrow once the lead is implanted comprises a flexible hinge coupling the finger to the insulative sheath, the flexible hinge biasing the finger out of the furrow and away from the insulative sheath, the finger further comprising a stylet lumen communicating with the insulative sheath lumen.

14. A medical electrical lead assembly according to claim 9 wherein the finger is positioned between approximately 6 cm. and 10 cm. from the second end of the lead body.

15. A medical electrical lead assembly according to claim 8 wherein the atrial electrode positioned between approximately 11 cm. and 16 cm. from the second end of the lead body.

16. A medical electrical lead assembly according to claim 9 wherein the finger is between approximately 8 mm. and 15 mm. in length.

* * * * *